(12) United States Patent
Topalian et al.

(10) Patent No.: US 9,279,011 B2
(45) Date of Patent: Mar. 8, 2016

(54) PHOSPHOPEPTIDES AS MELANOMA VACCINES

(75) Inventors: Suzanne L. Topalian, Brookeville, MD (US); Florence A Depontieu, Lyons (FR); Donald F. Hunt, Charlottesville, VA (US); Jeffrey Shabanowitz, Charlottesville, VA (US); Jie Qian, Somerset, NJ (US); Victor H. Engelhard, Crozet, VA (US); Angela Lee Zarling, Charlottesville, VA (US)

(73) Assignees: The Johns Hopkins University, Baltimore, MD (US); University of Virginia Patent Foundation, Charlottesville, VA (US)

( * ) Notice: Subject to any disclaimer, the term of this patent is extended or adjusted under 35 U.S.C. 154(b) by 377 days.

(21) Appl. No.: 13/318,821

(22) PCT Filed: May 4, 2010

(86) PCT No.: PCT/US2010/033530
§ 371 (c)(1),
(2), (4) Date: Apr. 2, 2012

(87) PCT Pub. No.: WO2010/129537
PCT Pub. Date: Nov. 11, 2010

(65) Prior Publication Data
US 2012/0177669 A1    Jul. 12, 2012

Related U.S. Application Data

(60) Provisional application No. 61/175,677, filed on May 5, 2009, provisional application No. 61/175,982, filed on May 6, 2009, provisional application No. 61/326,864, filed on Apr. 22, 2010.

(51) Int. Cl.
| | |
|---|---|
| *A61K 39/00* | (2006.01) |
| *A61K 47/00* | (2006.01) |
| *C07K 14/47* | (2006.01) |
| *G01N 33/574* | (2006.01) |
| *C12Q 1/68* | (2006.01) |
| *A61K 39/39* | (2006.01) |

(52) U.S. Cl.
CPC ......... *C07K 14/4748* (2013.01); *A61K 39/0011* (2013.01); *G01N 33/5743* (2013.01); *A61K 39/39* (2013.01); *A61K 2039/5154* (2013.01); *A61K 2039/5158* (2013.01)

(58) Field of Classification Search
None
See application file for complete search history.

(56) References Cited

U.S. PATENT DOCUMENTS

| | | | |
|---|---|---|---|
| 7,691,593 B2 * | 4/2010 | Pepicelli et al. | 435/7.23 |
| 2002/0044948 A1 | 4/2002 | Khleif et al. | |
| 2003/0228319 A1 | 12/2003 | Frantz et al. | |
| 2005/0202009 A1 * | 9/2005 | Kropshofer et al. | 424/144.1 |
| 2005/0277161 A1 | 12/2005 | Engelhard et al. | |

FOREIGN PATENT DOCUMENTS

| | | |
|---|---|---|
| WO | 03066820 A2 | 8/2003 |
| WO | 2008120202 A2 | 10/2008 |

OTHER PUBLICATIONS

Bioley et al (J. Immunol. 2006, 177: 6769-6779).*
Biddison and Martin (Curr. Prot. Immunol. 2000, A.11.1-A.11.7).*
Thibodeau (OncoImmunology 1:6, 908-916; Sep. 2012; © 2012 Landes Bioscience).*
Li et al. Structural Basis for the Presentation of Tumor-Associated MHC Class II restricted Phosphopeptides to CD4 (+) T Cells; In; J. Mol. Bio., Jun. 18, 2010 (epub: Apr. 24, 2010) vol. 399; p. 596-603.
Depontieu et al., Identification of tumor-associated MHC class II restricted phosphopeptides as targets for immunotherapy. PNAS, Jul. 21, 2009, vol. 106, No. 29, pp. 12073-12078.
International Search Report for PCT/US2011/033530 dated Jul. 4, 2010.

* cited by examiner

*Primary Examiner* — Michael Szperka
*Assistant Examiner* — Marianne Dibrino
(74) *Attorney, Agent, or Firm* — Banner & Witcoff, LTD.

(57) ABSTRACT

We characterized a total of 175 HLA-DR-associated phosphopeptides using sequential affinity isolation, biochemical enrichment, mass spectrometric sequencing and comparative analysis. Many were derived from source proteins which may have roles in cancer development, growth and metastasis. Most were expressed exclusively by either melanomas or transformed B cells, suggesting the potential to define cell type-specific phosphatome "fingerprints". We generated HLA-DRβ1*0101-restricted CD4+ T cells specific for a phospho-MART-1 peptide identified in two melanoma cell lines. These T cells showed specificity for phosphopeptide-pulsed antigen presenting cells as well as for intact melanoma cells. MHC II-restricted phosphopeptides recognizable by human CD4+ T cells are potential targets for cancer immunotherapy.

21 Claims, 7 Drawing Sheets

| | EBV | HLA-DRβ1* 0101† | other | IFN-γ (ng/ml) pMART-1 | HA | SI‡ |
|---|---|---|---|---|---|---|
| Exp.1 | 1087 | - | 07011, 1201 | 0.67 | 0.69 | 1.0 |
| | 1102 | - | 0401,1501/02 | 0.10 | 0.08 | 1.2 |
| | 1363 | + | none | 7.88 | 0.48 | 16.4 |
| | 2048 | + | 0404 | 7.59 | 0.24 | 31.4 |
| Exp.2 | 1088 | - | 0301,0401 | 0.07 | 0.05 | 1.6 |
| | 1558 | + | 1101 | 4.13 | 0.40 | 10.2 |
| | 2048 | + | 0404 | 5.03 | 0.25 | 20.2 |

(TABLE 1) CHARACTERISTICS OF HLA-DR-ASSOCIATED PHOSPHOPEPTIDES SELECTIVELY EXPRESSED BY MELANOMA CELLS

| SOURCE PROTEIN | LOCATION* | PHOSPHOPEPTIDE† | 1363-MEL§ | 2048-MEL§ | KNOWN PHOSPHOSITE |
|---|---|---|---|---|---|
| 1363-MEL AND 2048-MEL MELANOMA ANTIGEN RECOGNIZED BY T-CELLS 1/MART-1 | M | $_{100}$APPAYEKLpSAEQ$_{111}$ | + | - | N |
|  |  | $_{100}$APPAYEKLpSAEQSPP$_{114}$ | + | . |  |
|  |  | $_{100}$APPAYEKLpSAEQSPPP$_{115}$ | ++ | ++ |  |
|  |  | $_{100}$APPAYEKLpSAEQSPPPY$_{116}$ | + | + |  |
| TENSIN-3 | PM | $_{1433}$FVSKVMIGpSPKKV$_{1445}$ | - | +,+¶ | N |
|  |  | $_{1434}$VSKVMIGpSPKKV$_{1445}$ | ++,+¶ | +++,++¶ |  |
|  |  | $_{1437}$VMIGpSPKKV$_{1445}$ | +,+¶ | - |  |
| 1363-MEL ALONE MATRIX-REMODELING-ASSOCIATED PROTEIN 7 | PM | $_{142}$KYpSPGKLRGN$_{151}$ | + | - | N |
| 2048-MEL ALONE AMINO-TERMINAL ENHANCER OF SPLIT | N† | $_{176}$SKEDKNGHDGDTHQEDDGEKpSD$_{197}$ | - | ++ | N |
|  |  | $_{43}$GSALGGGGAGLSGRASGGAQpSPLRYLHV$_{71}$ | - | ++ |  |
| ANKYRIN REPEAT DOMAIN-CONTAINING PROTEIN 54 | UK | $_{46}$LGGGGAGLSGRASGGAQpSPLRYLHV$_{71}$ | - | + | Y |
|  |  | $_{58}$SGGAQpSPLRYLHVL$_{72}$ | - | + |  |
| ANOCTAMIN-8 | PM | $_{638}$EEGpSPTMVEKGLEPGVFTL$_{656}$ | - | + | N |
|  |  | $_{639}$EGpSPTMVEKGLEPGVFTL$_{656}$ | - | + |  |
|  |  | $_{640}$GpSPTMVEKGLEPGVFTL$_{656}$ | - | + |  |
| AP-3 COMPLEX SUBUNIT DELTA-1 | GM | $_{779}$EEMPENALPpSDEDDKDPNDPYRAL$_{802}$ | - | + | Y |
| CASEIN KINASE II SUBUNIT BETA | ER/G | $_{202}$QAASNFKpSPVKTIR$_{215}$ | - | + | Y |
|  |  | $_{203}$AASNFKpSPVKTIR$_{215}$ | - | + |  |
|  |  | $_{205}$SNFKpSPVKTIR$_{215}$ | - | + |  |
|  |  | $_{206}$NFKpSPVKTIR$_{215}$ | - | + |  |
|  |  | $_{207}$FKpSPVKTIR$_{215}$ | - | + |  |
| CLAUDIN-11 | PM | $_{191}$YYTAGSSpSPTHAKSAHV$_{207}$ | - | + | N |
|  |  | $_{196}$SSpSPTHAKSAHV$_{207}$ | - | + |  |
| EMERIN | NM | $_{117}$VRQpSVTSFPDADAFHHQ$_{133}$ | - | ++ | Y |
| FLJ20689 | UK | $_{471}$FKMPQEKpSPGYS$_{482}$ | - | ++ | N |
| INSULIN RECEPTOR SUBSTRATE 2 | PM | $_{1097}$RVApSPTSGVKR$_{1107}$ | - | + | Y |
| INTERLEUKIN 1 RECEPTOR ACCESSORY PROTEIN | PM | $_{543}$QVAMPVKKSPRRSpSSDEQGLSYSSLKNV$_{570}$ | - | ++ | N |
|  |  | $_{544}$VAMPVKKSPRRSpSSDEQGLSYSSLKNV$_{570}$ | - | + |  |
| LUC7-LIKE ISOFORM b | N | $_{353}$SSNGKMASRRpSEEKEAG$_{369}$ | - | + | Y |
|  |  | $_{353}$SSNGKMASRRpSEEKEAGEI$_{371}$ | - | + |  |
| MEMBRANE-ASSOCIATED PROGESTERONE RECEPTOR COMPONENT 1 | MIM/ERM | $_{172}$KEGEEPTVYpSDEEEPKDESARKND$_{195}$ | - | + | Y |
|  |  | $_{173}$EGEEPTVYpSDEEEPKDESARKND$_{195}$ | - | ++ |  |
| NF-KAPPA-B INHIBITOR-INTERACTING RAS-LIKE PROTEIN 2 | C† | $_{165}$ASKMTQPQSKSAFPLSRKNKGpSGpSLDG$_{191}$ | - | ++ | N |
| PROBABLE FIBROSIN-1 LONG TRANSCRIPT PROTEIN ISOFORM 2 | UK | $_{348}$APPPLVPAPRPSpSPPRGPGPARADR$_{372}$ | - | ++ | N |
| SMALL ACIDIC PROTEIN | UK | $_{2}$SAARESHPGVKRSApSPDDDLG$_{23}$ | - | + | Y |
|  |  | $_{2}$(AcS)AARESHPGVKRSApSPDDDLG$_{23}$ | - | +++ |  |
| SYNAPTOJANIN-170 | C | $_{1561}$ASKApSPTLDFTER$_{573}$ | - | + | Y |
| TETRASPANIN-10 | PM | $_{4}$GERpSPLLSQETAGQKP$_{19}$ | - | ++ | N |
|  |  | $_{4}$GERpSPLLSQETAGQKPL$_{20}$ | - | ++ |  |
|  |  | $_{5}$ERpSPLLSQETAGQKP$_{19}$ | - | ++ |  |
|  |  | $_{5}$ERpSPLLSQETAGQKPL$_{20}$ | - | + |  |
| TRANSMEMBRANE PROTEIN 184C | PM/C | $_{424}$TIGEKKEPpSDKSVDS$_{438}$ | - |  | N |

FIG. 4

SEQUENCE LISTING

```
<160> NUMBER OF SEQ ID NOS: 24

<210> SEQ ID NO 1
<211> LENGTH: 118
<212> TYPE: PRT
<213> ORGANISM: Homo sapiens

<400> SEQUENCE: 1

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 2
<211> LENGTH: 9
<212> TYPE: PRT
<213> ORGANISM: Homo sapiens

<400> SEQUENCE: 2

Ala Pro Pro Ala Tyr Glu Lys Leu Ser
1               5
```

-continued

<210> SEQ ID NO 3
<211> LENGTH: 9
<212> TYPE: PRT
<213> ORGANISM: Homo sapiens

<400> SEQUENCE: 3

Pro Pro Ala Tyr Glu Lys Leu Ser Ala
1               5

<210> SEQ ID NO 4
<211> LENGTH: 9
<212> TYPE: PRT
<213> ORGANISM: Homo sapiens

<400> SEQUENCE: 4

Pro Ala Tyr Glu Lys Leu Ser Ala Glu
1               5

<210> SEQ ID NO 5
<211> LENGTH: 9
<212> TYPE: PRT
<213> ORGANISM: Homo sapiens

<400> SEQUENCE: 5

Ala Tyr Glu Lys Leu Ser Ala Glu Gln
1               5

<210> SEQ ID NO 6
<211> LENGTH: 9
<212> TYPE: PRT
<213> ORGANISM: Homo sapiens

<400> SEQUENCE: 6

Tyr Glu Lys Leu Ser Ala Glu Gln Ser
1               5

<210> SEQ ID NO 7
<211> LENGTH: 9
<212> TYPE: PRT
<213> ORGANISM: Homo sapiens

<400> SEQUENCE: 7

Glu Lys Leu Ser Ala Glu Gln Ser Pro
1               5

<210> SEQ ID NO 8
<211> LENGTH: 9
<212> TYPE: PRT
<213> ORGANISM: Homo sapiens

<400> SEQUENCE: 8

Lys Leu Ser Ala Glu Gln Ser Pro Pro
1               5

<210> SEQ ID NO 9
<211> LENGTH: 9
<212> TYPE: PRT
<213> ORGANISM: Homo sapiens

<400> SEQUENCE: 9

Leu Ser Ala Glu Gln Ser Pro Pro Pro
1               5

<210> SEQ ID NO 10

```
<211> LENGTH: 9
<212> TYPE: PRT
<213> ORGANISM: Homo sapiens

<400> SEQUENCE: 10

Ser Ala Glu Gln Ser Pro Pro Pro Tyr
1               5

<210> SEQ ID NO 11
<211> LENGTH: 20
<212> TYPE: PRT
<213> ORGANISM: Homo sapiens

<400> SEQUENCE: 11

Val Pro Asn Ala Pro Pro Ala Tyr Glu Lys Leu Ser Ala Glu Gln Ser
1               5                   10                  15

Pro Pro Pro Tyr
            20

<210> SEQ ID NO 12
<211> LENGTH: 12
<212> TYPE: PRT
<213> ORGANISM: Homo sapiens

<400> SEQUENCE: 12

Pro Asn Ala Pro Pro Ala Tyr Glu Lys Leu Ser Ala
1               5                   10

<210> SEQ ID NO 13
<211> LENGTH: 12
<212> TYPE: PRT
<213> ORGANISM: Homo sapiens

<400> SEQUENCE: 13

Asn Ala Pro Pro Ala Tyr Glu Lys Leu Ser Ala Glu
1               5                   10

<210> SEQ ID NO 14
<211> LENGTH: 12
<212> TYPE: PRT
<213> ORGANISM: Homo sapiens

<400> SEQUENCE: 14

Ala Pro Pro Ala Tyr Glu Lys Leu Ser Ala Glu Gln
1               5                   10

<210> SEQ ID NO 15
<211> LENGTH: 15
<212> TYPE: PRT
<213> ORGANISM: Homo sapiens

<400> SEQUENCE: 15

Ala Pro Pro Ala Tyr Glu Lys Leu Ser Ala Glu Gln Ser Pro Pro
1               5                   10                  15

<210> SEQ ID NO 16
<211> LENGTH: 16
<212> TYPE: PRT
<213> ORGANISM: Homo sapiens

<400> SEQUENCE: 16

Ala Pro Pro Ala Tyr Glu Lys Leu Ser Ala Glu Gln Ser Pro Pro Pro
1               5                   10                  15
```

<210> SEQ ID NO 17
<211> LENGTH: 17
<212> TYPE: PRT
<213> ORGANISM: Homo sapiens

<400> SEQUENCE: 17

Ala Pro Pro Ala Tyr Glu Lys Leu Ser Ala Glu Gln Ser Pro Pro
1               5                   10                  15

Tyr

<210> SEQ ID NO 18
<211> LENGTH: 12
<212> TYPE: PRT
<213> ORGANISM: Homo sapiens

<400> SEQUENCE: 18

Pro Pro Ala Tyr Glu Lys Leu Ser Ala Glu Gln Ser
1               5                   10

<210> SEQ ID NO 19
<211> LENGTH: 12
<212> TYPE: PRT
<213> ORGANISM: Homo sapiens

<400> SEQUENCE: 19

Pro Ala Tyr Glu Lys Leu Ser Ala Glu Gln Ser Pro
1               5                   10

<210> SEQ ID NO 20
<211> LENGTH: 12
<212> TYPE: PRT
<213> ORGANISM: Homo sapiens

<400> SEQUENCE: 20

Ala Tyr Glu Lys Leu Ser Ala Glu Gln Ser Pro Pro
1               5                   10

<210> SEQ ID NO 21
<211> LENGTH: 12
<212> TYPE: PRT
<213> ORGANISM: Homo sapiens

<400> SEQUENCE: 21

Tyr Glu Lys Leu Ser Ala Glu Gln Ser Pro Pro Pro
1               5                   10

<210> SEQ ID NO 22
<211> LENGTH: 12
<212> TYPE: PRT
<213> ORGANISM: Homo sapiens

<400> SEQUENCE: 22

Ala Pro Pro Ala Tyr Glu Lys Leu Ser Ala Glu Gln
1               5                   10

<210> SEQ ID NO 23
<211> LENGTH: 15
<212> TYPE: PRT
<213> ORGANISM: Homo sapiens

<400> SEQUENCE: 23

Ala Pro Pro Ala Tyr Glu Lys Leu Ser Ala Glu Gln Ser Pro Pro
1               5                   10                  15

```
<210> SEQ ID NO 24
<211> LENGTH: 16
<212> TYPE: PRT
<213> ORGANISM: Homo sapiens

<400> SEQUENCE: 24

Ala Pro Pro Ala Tyr Glu Lys Leu Ser Ala Glu Gln Ser Pro Pro Pro
1               5                   10                  15
```

PHOSPHOPEPTIDES AS MELANOMA VACCINES

This invention was made with government support under grant nos. AI033993 and CA134060 awarded by the National Institutes of Health. The government has certain rights in the invention.

TECHNICAL FIELD OF THE INVENTION

This invention is related to the area of immunotherapy and immunodiagnostics. In particular, it relates to cancer immunotherapy and immunodiagnostics.

BACKGROUND OF THE INVENTION

Immunotherapies directed against currently defined tumor-associated or tumor-specific antigens can enhance anti-tumor immunity in patients, as detected with in vitro immune monitoring, and yet have had limited clinical success (1). One reason may be the nature of the targeted antigens, the majority of which are proteins overexpressed in tumor cells but not essential to maintaining their malignant phenotype.

Phosphorylation is the most common and ubiquitous form of enzyme-mediated post-translational protein modification, and transient phosphorylation of intracellular signaling molecules regulates cellular activation and proliferation (2). Phosphorylation cascades are often dysregulated during malignant transformation, leading to uncontrolled proliferation, invasion of normal tissues, and distant metastasis (3, 4). Limited but growing evidence has shown that tumor-associated phosphoproteins processed intracellularly through an endogenous pathway can give rise to phosphopeptides complexed to MHC I molecules which are displayed on the cell surface (5, 6). CD8+ T cells immunized to specifically recognize these phosphopeptides are also capable of recognizing intact human tumor cells, suggesting that phosphopeptides may represent a new class of targets for cancer immunotherapy (5, 6) (ALZ and VHE, unpublished data). In these studies and others, T cell discrimination of the phosphopeptide versus its non-phosphorylated counterpart was observed, indicating that phosphorylation can influence peptide immunogenicity (5-13). Recent crystal structural definition of phosphorylated peptide-HLA-A2 complexes demonstrated direct and indirect interactions of the phosphoresidue with the MHC molecule, often significantly increasing the affinity of the phosphopeptide for MHC I. Additionally, phosphoresidues were solvent-exposed, suggesting the potential for direct interactions with the T cell receptor (TCR) (14, 15).

Mounting evidence indicates that MHC II-restricted CD4+ T lymphocytes are a critical component of anti-tumor immunity, and that their activation and recruitment may be required to optimize cancer immunotherapies (16, 17). A variety of post-translational modifications have been identified on naturally processed MHC class II-associated epitopes. These include N- and O-linked glycosylation, N-terminal acetylation, nitration, deamidation, and deimination/citrullination (18). Although an early attempt to detect phosphorylation on class II MHC peptides met with failure (5), new technology has now made it possible to observe this modification as well (19). Here we demonstrate the existence of MHC II-associated phosphopeptides on human melanoma cells and EBV-transformed B (EBV-B) lymphoblasts, and we define and compare the sequences of phosphopeptides complexed to HLA-DR molecules on two autologous pairs of melanoma and B cell cultures. Furthermore, we show for the first time the ability of human CD4+ T cells to specifically recognize phosphoepitopes displayed in the context of MHC II molecules, using the example of an HLA-DRβ1*0101-restricted phospho-MART-1 peptide isolated independently from two melanoma cell lines. These findings suggest that tumor-associated phosphopeptides provide targets for CD4+ as well as CD8+ T cells, potentially enabling the development of new immunotherapeutic strategies.

There is a continuing need in the art to identify new therapeutic targets and new markers of disease.

SUMMARY OF THE INVENTION

According to one aspect of the invention an isolated phosphopeptide is provided. It comprises between 9 and 30 contiguous amino acids selected from SEQ ID NO: 1 (MART-1) including the serine at position 108 of MART-1 which is phosphorylated.

According to another aspect of the invention a method is provided for immunizing a mammal to diminish the risk of, the growth of, or the invasiveness of a melanoma. A composition comprising a phosphopeptide is administered to the mammal. The phosphopeptide comprises between 9 and 30 contiguous amino acids selected from SEQ ID NO: 1 (MART-1) including the serine at position 108 of MART-1 which is phosphorylated. CD4+ T cells in the mammal are thereby activated.

According to another aspect of the invention a method is provided for stimulating CD4+ T cells. T cells are contacted in vitro with an isolated phosphopeptide. The phosphopeptide comprises between 9 and 30 contiguous amino acids selected from SEQ ID NO: 1 (MART-1) including the serine at position 108 of MART-1 which is phosphorylated. CD4+ T cells are thereby stimulated.

According to yet another aspect of the invention a method is provided for characterizing a body sample. A sample isolated from a patient is contacted with an antibody that specifically binds to a phosphopeptide that comprises between 9 and 30 contiguous amino acids selected from SEQ ID NO:1 (MART-1) including the serine at position 108 of MART-1 which is phosphorylated. The antibody does not bind to a polypeptide consisting of the same amino acid sequence but devoid of phosphorylation. Antibody bound to the sample is measured or detected.

According to still another aspect of the invention a binding molecule is provided. The binding molecule comprises an antigen-binding region of an antibody. The binding molecule specifically binds to a phosphopeptide that comprises between 9 and 30 contiguous amino acids selected from SEQ ID NO:1 (MART-1) including the serine at position 108 of MART-1 which is phosphorylated. The binding molecule does not bind to a polypeptide consisting of the same amino acid sequence but devoid of phosphorylation.

According to another aspect a kit for measuring a phosphopeptide is provided. The phosphopeptide comprises between 9 and 30 contiguous amino acids selected from SEQ ID NO: 1 (MART-1) including the serine at position 108 of MART-1 which is phosphorylated. The kit comprises a molecule comprising an antigen-binding region of an antibody. The molecule specifically binds to the phosphopeptide and does not bind to a polypeptide consisting of the same amino acid sequence but devoid of phosphorylation.

According to still another aspect a method is provided. Dendritic cells are contacted in vitro with an isolated phosphopeptide comprising between 9 and 30 contiguous amino acids selected from SEQ ID NO:1 (MART-1) including the serine at position 108 of MART-1 which is phosphorylated. The dendritic cells are thereby loaded with the phosphopeptide.

These and other embodiments which will be apparent to those of skill in the art upon reading the specification as a whole provide the art with tools and methods for characterizing, detecting, prognosing, monitoring, treating, and reducing the risk of primary cancers and metastases.

BRIEF DESCRIPTION OF THE DRAWINGS

(FIG. 2A) An anti-HLA-DR mAb inhibits T cell recognition of peptide-pulsed 2048-EBV. (FIG. 2B) T cells recognize pMART-1 peptide presented by allogeneic DR1+ APC. T cell IFN-γ secretion measured by ELISA. †: Genotype; EBV-B cell expression of HLA-DR1 was confirmed by flow cytometry. ‡SI: Stimulation index, ratio of IFN-γ secretion in response to pMART-1 versus the irrelevant HA peptide. SI>2 is considered significant.

FIG. 4: (Table 1) provides a table showing characteristics of HLA-DR-associated phosphopeptides selectively expressed by melanoma cells. Protein sources were determined by searching peptide sequences against the nr and refseq databases for human proteins (using BLAST at the NCBI website). * Localization: C, Cytoplasm; E, Endosome; ER, Endoplasmic reticulum; ERM, Endoplasmic reticulum membrane; G, Golgi; GM, Golgi membrane; LM, Lysosome membrane; M, Membrane; MIM, Microsomal membrane; MTM, Mitochondrial membrane; N, Nucleus; NM, Nuclear membrane; PM, Plasma membrane; UK, Unknown. †: Hypothetical localization. ‡: pS/T/Y correspond to serine, threonine, or tyrosine-associated phosphorylated residues, respectively; italics, the exact site of phosphorylation could not be determined. §: Abundance: −, not detected; +, <6 copies per cell; ++, 6-50 copies per cell; +++, 51-140 copies per cell; nm, not measured. ¶: Abundance of peptide containing Met and Met$^{ox}$, respectively.

DETAILED DESCRIPTION OF THE INVENTION

Figure 1:
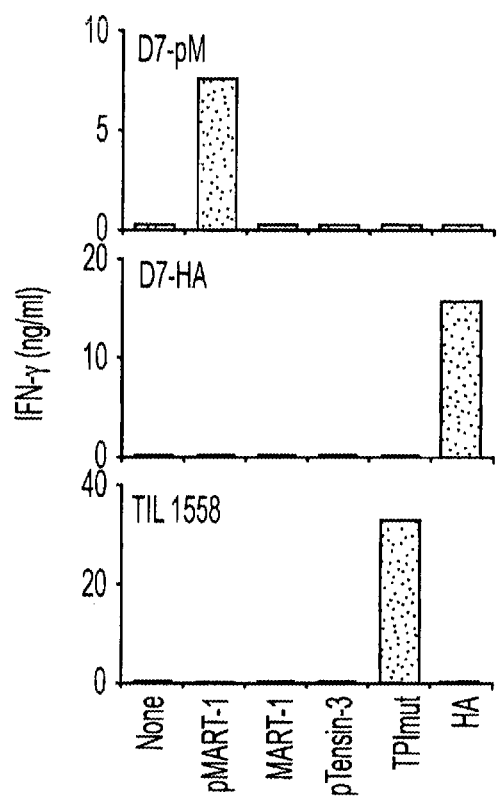
FIG. 1 shows that CD4+ T cells specifically recognize the melanoma-associated phosphopeptide pMART-1. Peptide recognition by D7-pM T cells raised against pMART-1 (upper) is compared to recognition by CD4+ HA-specific cells from the same patient (middle), or by TPImut-specific CD4+ TIL1558 (lower). Peptides were pulsed onto HLA-DR1+ 2048-EBV cells. Similar results were obtained using DR1+ 1363-EBV as APC (not shown).

We have developed markers and immunological targets for melanoma. We have investigated phosphopeptides, a category of tumor-derived epitopes linked to proteins with vital cellular functions. We demonstrate the ability of human CD4+ T cells to discriminate between a phosphoresidue and its non-phosphorylated counterpart. Using sequential affinity isolation, biochemical enrichment, mass spectrometric sequencing, and comparative analysis, we characterized a total of 175 HLA-DR-associated phosphopeptides. Most were expressed exclusively by either melanomas or transformed B cells, suggesting the potential to define cell type-specific phosphatome "fingerprints". We generated HLA-DRβ1*0101-restricted CD4+ T cells specific for a phospho-MART-1 peptide identified in two melanoma cell lines. These T cells showed specificity for phosphopeptide-pulsed antigen presenting cells as well as for intact melanoma cells. The MHC II-restricted phosphopeptides recognizable by human CD4+ T cells are attractive targets for cancer immunotherapy.

Isolated phosphopeptides are those which have been extracted from cells or which have been synthesized. Typically they are in a partially or almost complete state of purity. The phosphopeptides comprises at least 50%, at least 60%, at least 70%, at least 80%, at least 90%, or at least 95% by weight of the polypeptides present in such a state. Usually they are free of other polypeptides and/or other phosphopeptides. Often they are free of human cells. The phosphopeptides may have between 9 and 30 contiguous amino acids selected from SEQ ID NO: 1. In particular, the phosphopeptides contain the serine at residue 108 which is phosphorylated. They may have additional amino acids which are derived from other proteins located on the N-terminal or the C-terminal side. They may be attached via covalent or non-covalent bonds to solid supports such as beads, wells, resins, or other surfaces. They may be conjugated to other bioactive moieties, such as toxins. Examples of phosphopeptides which may be used include those consisting of residues 100-108, residues 101-109, residues 102-110, residues 103-111, residues 104-112, residues 105-113, residues 106-114, residues 107-115, and residues 108-116. Others may comprise or contain residues 100-108, residues 101-109, residues 102-110, residues 103-111, residues 104-112, residues 105-113, residues 106-114, residues 107-115, and residues 108-116. Still others may comprise residues 97-116, residues 99-110, residues 100-111, residues 100-114, residues 100-115, and residues 100-116. The phosphopeptides may contain additional residues or may consist of these recited residues.

The phosphopeptides may be used in complexes. One particularly useful complex is with HLA-DR1 proteins. One particular such protein which may be useful is HLA-DRβ*0101. These proteins may be in monomer, dimer, trimer, tetramer, or higher order multimer forms. The complexes may form naturally, based on inherent properties of complex partners, or they may be designed to multimerize using specific reagents to bring monomers or dimers together. Such reagents include, without limitation, immunoglobulin molecules, biotin, avidin, streptavidin, and the like. The phosphopeptides may be covalently or non-covalently bound to the HLA-DR1 proteins. The complexes or components may be conjugated to a detectable label (e.g., a fluorescent moiety, a radionuclide, or an enzyme that catalyzes a reaction resulting in a product that absorbs or emits light of a defined wavelength). These can be used inter alia to quantitate T cells from subject (e.g., a human patient) bearing cell surface receptors that are specific for, and therefore will bind, the complexes. Relatively high numbers of such T cells are likely to be diagnostic of a melanoma. One can monitor the relative numbers of complex-binding T cells as a means of assessing the course of a disease or the efficacy of therapy. The complexes may be used to stain or label T cells.

Notwithstanding the desired purity or isolation of phosphopeptides, they may be purposely mixed with other protein or phosphopeptide species to achieve desired properties. Combinations and admixtures may achieve synergistic results. A mixture may be used to achieve better properties in a single individual, for example increased avidity, Alternatively, a mixture may be used to achieve wider applicability in a population of humans. A mixture may also be desired to impart a combination of distinct activities to a composition or preparation. Other polypeptides which may be admixed with MART-1 polypeptides include both phosphorylated and non-phosphorylated polypeptides. Adjuvants for stimulating immune responses may be used in admixture. Such adjuvants include without limitation, incomplete Freund's adjuvant, QS21, Toll-receptor stimulants, LPS, and other generic and proprietary adjuvants. Agents for inhibiting regulatory T cells may be used in admixture. Most agents which can be used in admixtures can also be administered separately to the same individual. Typically such separate administrations will occur within a limited window of time, such as within a month, within a week, within 4 days, within 2 days, within 24 hours, within 12 hours, or within 2 hours.

Compositions for administration to a human may be packaged in a single container or in a divided container. Packaging may include instructions for administration or for analytical testing. Other reagents or therapeutic agents or immunological agents may also be packaged together, forming kits. Therapeutic or prophylactic compositions may be packaged with delivery devices which may optionally be pre-loaded.

Compositions comprising phosphopeptides or the phosphopeptides themselves may be administered to a mammal, including a human, using any available means of delivery. Many means of delivering immunological preparations are known in the art and any of these may be used. Without limitation, one could use intradermal, intravenous, intramuscular, subcutaneous, intraperitoneal injections. The preparations can be administered without injection, such as by intranasal or intrabronchial inhalation or instillation. The compositions can be administered to persons at risk of developing a melanoma or other cancer which expresses MART-1 phosphopeptides in order to reduce the risk of, reduce the severity of, or delay the onset of such a cancer. The administration may be to a person who already has such as cancer in order to inhibit progression, growth, and/or metastasis of the cancer. Mammals that can be prophylactically or therapeutically treated include humans, pets, farm animals, food animals, laboratory animals. Animal models of human disease may be so treated.

One method of using the phosphopeptides involves the in vitro simulation or activation of T cells, in particular $CD4^+$ T cells. For example, T cells can be removed from a patient and fractionated or not to provide a preparation comprising $CD4^+$ T cells. Stimulated or activated T cells may be transfused back into the same patient (autologous) or into other patients. Similarly, the phosphopeptides may be contacted with dendritic cells in vitro to load them with polypeptides for presentation to T cells. The loaded dendritic cells may form compositions that may be transfused or injected into patients to enhance or stimulate a T cell immune response.

Antibody molecules and antibody derivatives are well known in the art and include polyclonal and monoclonal antibodies, humanized antibodies, chimeric antibodies, single chain variable regions, Fab', and Fab2. Any molecules that include an antigen-binding region of an antibody can be used for specific binding to a MART-1 phosphopeptide. The desirable specificity is that the binding molecules will recognize and bind to the phosphopeptide but not to the corresponding non-phosphorylated polypeptide. Antibodies, similar to $CD4^+$ T cells, can recognize this difference. Antibodies can be packaged as kits, in a single divided or undivided container. They kits may contain instructions, buffers, control samples, solid supports, labels, secondary antibodies, etc, as are known in the art. The kits may be used among other purposes to monitor a disease, detect a disease, or monitor efficacy of therapy.

Antibody molecules and other binding molecules can be used analytically. For example, they can be used to detect the presence or absence of MART-1 phosphopeptides in a patient sample. They can be used to detect the level of MART-1 phosphopeptides in a patient sample. Quantitative or non-quantitative methods may be used to assess binding.

Analytic methods for determining the presence of MART-1 phosphopeptides can be used on samples obtained from a patient or test subject. Suitable samples include without limitation, biopsies, lymph nodes, blood, serum, plasma, saliva, lymph, sputum, urine, cerebrospinal fluid, and stool. The samples may be from normal tissue or cancer tissue. A huge variety of immunological assay techniques are known in the art and any of these may be used with the phosphopeptide-binding molecules.

The methods and compositions of the invention may be used and/or derived from humans or non-human animals. Appropriate mammals include pets, farm animals, companion animals. Specific examples include dogs, cats, horses, cows, sheep, pigs, guide dogs.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

T Cell Recognition of the Candidate Phosphopeptide B-Raf mut$^{pT599}$

To assess the potential for human CD4$^+$ T cells to specifically discriminate phosphoresidues, we first explored the candidate mutant melanoma antigen B-Raf$^{V600E}$ (B-Raf mut) shared by 60% of melanomas (20). The somatic V600E mutation constitutively activates the B-Raf serine-threonine kinase and hence the MAPK cascade, presumably by mimicking a phosphorylation event. V600E is juxtaposed to the known dominant phosphosite T599. We previously reported that in vitro stimulation of melanoma patient peripheral blood mononuclear cells (PBMC) with a non-phosphorylated 29-mer candidate B-Raf mut peptide generated B-Raf mut-specific HLA-DRβ1*0404-restricted CD4$^+$ T cells that did not cross-react with the wild type peptide (B-Raf wt) and that specifically recognized HLA compatible melanoma cells expressing B-Raf mut(21). To investigate the fine specificity of MHC II-restricted CD4$^+$ T cells for phosphate moieties, T cells raised against non-phosphorylated B-Raf mut were assessed for recognition of synthetic B-Raf mut$^{pT599}$. These T cells failed to react to the phosphorylated peptide. Conversely, we used the monophosphorylated peptide B-Raf mut$^{pT599}$ to sensitize new CD4$^+$ T cell cultures, which specifically recognized both B-Raf mut$^{pT599}$ and B-Raf wt$^{pT599}$ but not their non-phosphorylated counterparts. Using anti-MHC blocking antibodies and HLA matched or mismatched allogeneic antigen presenting cells (APC), we characterized HLA-DR11 as the restricting MHC allele for T cell recognition of the B-Raf phosphopeptides (data not shown). T cells sensitized in vitro against synthetic B-Raf mut$^{pT599}$ failed to recognize melanoma cells, suggesting that the hypothetical epitope might not be generated by intracellular processing, or that the conformation of the exogenously pulsed peptide-MHC complex failed to reproduce the conformation of a naturally processed epitope (22). Importantly however, these experiments demonstrate for the first time that, similar to MHC I-restricted CD8$^+$ T cells, human CD4$^+$ T cells are capable of specifically recognizing phosphopeptides complexed to MHC II molecules, and that the phosphoresidue can be a critical determinant of recognition.

Example 2

Identification and Characterization of HLA-DR-Associated Phosphopeptides

To identify naturally processed tumor-associated MHC II-restricted phosphopeptides as potential targets for immune recognition, we affinity isolated HLA-DR-peptide complexes from 2 cultured melanoma lines (1363-mel and 2048-mel) and their autologous EBV-B cell counterparts (1363-EBV and 2048-EBV). These cell lines were selected because they constitutively express significant levels of common HLA-DR molecules, as assessed with flow cytometric analysis using the pan-DR mAb L243 and HLA allele-specific mAbs (not shown). By HLA genotyping, 2048-mel and 2048-EBV contain HLA-DRβ1*0101, which is found in 31% of melanoma patients (23); DRβ1*0404, found in 6.5% of patients (23); and DRβ4*0103. Notably, 1363-mel and -EBV contain a single DR molecule, HLA-DR DRβ1*0101, affording an opportunity to isolate phosphopeptides with unambiguous HLA allele restriction. Patients 2048 and 1363 share HLA-DR DRβ1*0101, enabling the possibility of finding commonly expressed peptides on cell lines from both patients.

A total of 175 phosphopeptides were sequenced from the 4 cell lines (Table 1). Of note, this analysis does not account for peptides containing mutations, which would not be detected by existing search algorithms (see Materials and Methods). Twenty-three phosphopeptides were isolated from 2 or more cell lines, yielding a total of 150 unique phosphopeptides. Similar to non-phosphorylated MHC II-associated epitopes, the average length of the phosphorylated peptides was 16 amino acids (range 8-28) (24). Also characteristic of MHC II epitopes, 78% (117 of 150 sequences) were found within nested sets, defined as groups of peptides sharing core sequences but having distinct N- and C-termini. Most phosphopeptides were specifically expressed by either melanomas (FIG. 4) or EBV-B cells, although some were expressed by both cell types. Only 23 phosphopeptide sequences from 7 source proteins were identified from 1363-mel, while a larger number of phosphopeptide sequences (65) and source proteins (28) were identified from 2048-mel cells. The smaller number of sequences isolated from 1363-mel likely reflects the significantly lower expression of HLA-DR molecules by these cells as well as their expression of a single DR allele. Thirty-nine phosphopeptide sequences from 15 proteins, and 48 phosphopeptides from 20 proteins, were identified from 1363-EBV and 2048-EBV B cells, respectively. As might be anticipated because patients 1363 and 2048 share the HLA-DRβ1*0101 allele, phosphopeptides common to both patients occurred, including those found in both melanomas (melanoma antigen recognized by T-cells 1 (MART-1) and tensin-3, FIG. 4) or in both EBV-B cell lines (CD20). Experiments are in progress with melanomas and EBV-B cells generated from other patients, to better define cell type-specific phosphatome "fingerprints" and potential immunotherapeutic targets specific for melanomas or EBV-associated malignancies.

Phosphosites were assigned unambiguously for 96% of the 175 phosphopeptides sequenced in this study. Phosphopeptides contained only one phosphorylated residue, with the exception of a phosphopeptide derived from frizzled 6 in 1363-mel, which contained 2 phosphoresidues. Among a total of 57 defined phosphosites (accounting for redundancy in nested peptide sets), phosphate moieties were bound to serine, threonine or tyrosine residues in 93.0%, 5.3%, and 1.7% of cases, respectively. Interestingly, these frequencies are similar to those found in the HeLa cell-derived phosphoproteome (86.4%, 11.8%, and 1.8%, respectively (2)) suggesting that there is no significant bias in the processing or MHC II binding of peptides containing a particular phosphoresidue. Of note, studies have not identified MHC I-associated phosphopeptides containing phosphotyrosine residues; this may be explained by the generally low frequency of this post-translational modification, as well as by the relatively small number of phosphopeptides isolated in our earlier study compared to the current report (36 vs. 175 phosphopeptides, respectively (6)). Sixty percent (32 of 53) of the source proteins for the phosphopeptides described in this report are known to be phosphorylated. However only 17 of the 57 defined phosphosites (29.8%) had been previously identified (Table 1).

The 150 unique phosphopeptides listed in Table 1 and elsewhere are derived from a total of 53 different protein sources representing all cellular compartments, although transmembrane proteins predominate as would be expected for MHC II-associated peptides processed through the endosomal/lysosomal pathway. For those proteins located in the plasma membrane, the isolated phosphopeptides emanate from the cytoplasmic tail region. The processing of cytosolic and nuclear proteins via the MHC II pathway does not fit the "classical" model of antigen processing. However, mounting evidence suggests that autophagy, a stress-activated process operational in intracellular protein turnover, may play a critical role in shunting cytoplasmic proteins into the lysosomal compartment, thus influencing the MHC II-peptide repertoire (26, 27). Importantly, the majority of source proteins for the phosphopeptides found in this study are known to support vital biological functions such as metabolism, cell cycle regulation and intracellular signaling, and they may have important roles in cancer development, growth and metastasis. Thus, the derivative phosphopeptides may provide functionally relevant targets for immunotherapy.

Analyzing the abundance of the isolated phosphopeptides revealed ≤50 copies per cell, with rare exceptions (sequestosome-1 in 1363-mel, small acidic protein and tensin-3 in 2048-mel, and CD20 in 2048-EBV were present at 51-140 copies/cell). In fact, many phosphopeptides were found to be expressed at less than 6 copies/cell (FIG. 4). This highlights the exquisite sensitivity of the mass spectrometric methods used for detection. Because T cell responses may be activated by fewer than 10 peptide-MHC complexes per cell, the phosphopeptides described in this report are potentially immunogenic (28-30).

Example 3

Specific CD4+ T Cell Recognition of Phospho-MART-1

To assess the ability of human CD4+ T cells to specifically recognize tumor-associated phosphopeptides, we selected the MART-1$_{100-111}$ phosphopeptide (pMART-1, containing pS108) for further study. As shown in FIG. 4, a nested set of phosphopeptides derived from the C-terminus of MART-1 was eluted from both 1363- and 2048-mel which share HLA-DR DRβ1*0101, but not from the autologous EBV-B cell lines. Because of its selective expression pattern in cells of the melanocytic lineage, including normal melanocytes and melanoma cells, MART-1 (also termed Melan-A) is an important target of immunotherapeutic approaches for the treatment of melanoma including vaccines and adoptive T cell transfer (31, 32) This transmembrane protein, which is localized to melanosomes and functions to regulate mammalian pigmentation (33), was not known to be phosphorylated prior to the current report. However, several non-phosphorylated MHC class I- and II-restricted immunogenic epitopes have been identified in MART-1, spanning the entire protein (34-38). Some have provided the basis for synthetic melanoma peptide vaccines.

Fresh PBMC from melanoma patient D7, with the MHC II genotype HLA-DRβ1*01, HLA-DQβ1*0501, were repeatedly stimulated in vitro with the pMART-1 peptide under microculture conditions. Following several rounds of stimulation, the CD4+ microculture designated D7-pM specifically secreted IFN-γ (FIG. 1) and GM-CSF (data not shown) in response to the pMART-1 peptide, but not to the non-phosphorylated MART-1 peptide pulsed onto DR1-expressing APC. In titration experiments, pMART-1 could be recognized at concentrations <1 µM (not shown). As shown in FIG. 1, the tensin-3$_{1434-1445}$ phosphopeptide (pTensin-3), also eluted from 1363-mel, was not recognized by D7-pM T cells nor were other peptides having high affinity for HLA-DR1, including TPImut and HA. Conversely, CD4+ T cells specific for TPImut or HA secreted cytokines in response to their cognate epitopes but were not stimulated by pMART-1. These data suggest that CD4+ D7-pM T cells specifically recognize pMART-1 and that the phosphorylated serine residue is a critical determinant of recognition.

Figures 2A, 2B:
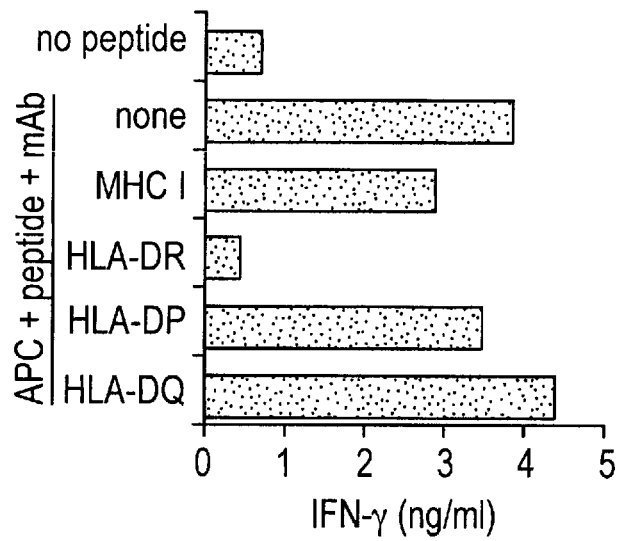
FIG. 2A-2B show HLA-DR1β1*0101 restriction of D7-pM CD4+ T cells specific for the pMART-1 peptide.
Figure 3:
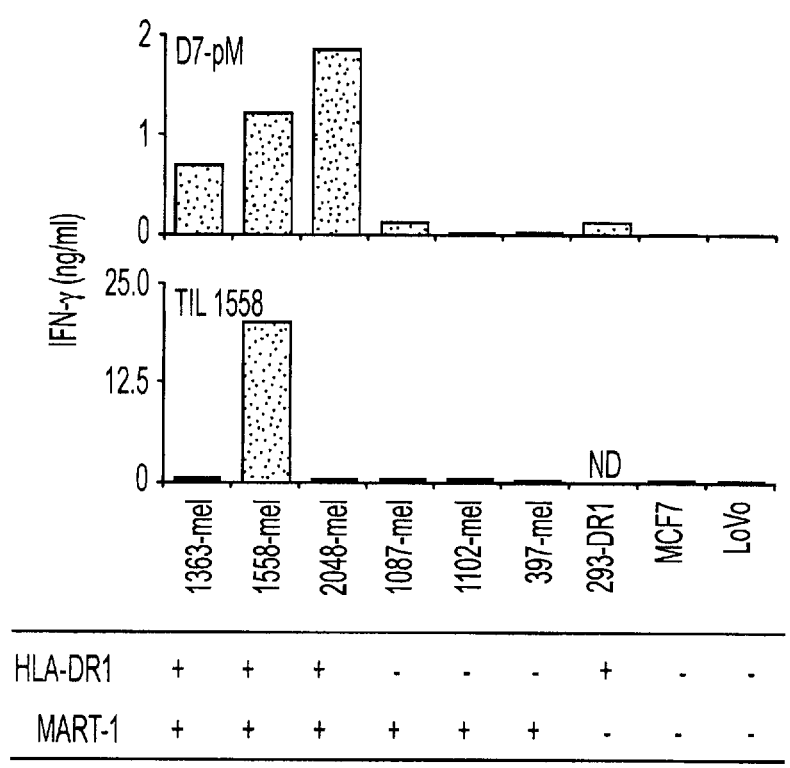
FIG. 3: D7-pM T cells specific for pMART-1 peptide recognize allogeneic intact melanoma cells expressing MART-1 and HLA-DRβ1*0101 (upper). In comparison, DR1-restricted CD4+ TIL 1558 are specific for autologous melanoma cells expressing the unique tumor antigen TPImut (middle; 39). HLA-DR1 expression was determined by flow cytometry (bottom). MART-1 expression was determined by recognition from HLA-A2-restricted MART-1 TCR-transduced T cells, intracellular staining with a MART-specific mAb (42), and/or Northern blotting (32) (bottom). ND, not done.

A nested set of four MART-1 phosphopeptides was eluted from 1363-mel and 2048-mel, sharing HLA-DRβ1*0101 (FIG. 4). Because phosphopeptides complexed to MHC molecules were affinity-eluted on an anti-HLA-DR column, and because HLA-DRβ1*0101 is the only DR molecule contained in 1363-mel by genotyping, we hypothesized that HLA-DRβ1*0101 was the restriction element for pMART-1 recognition by CD4+ D7-pM T cells. This was investigated with two complimentary approaches: anti-MHC mAbs were used to inhibit T cell recognition of peptide-pulsed APC, and a panel of allogeneic APC with diverse HLA types was used to present pMART-1 to T cells (FIG. 2). T-cell recognition of DR1+ 2048-EBV pulsed with pMART-1 was significantly inhibited by mAb directed against HLA-DR (L243) but not against HLA-DQ, HLA-DP, or class I MHC (FIG. 2A). Furthermore, D7-pM T cells specifically recognized the pMART-1 peptide only when pulsed onto allogeneic EBV-B cells sharing HLA-DRβ1*0101 (FIG. 2B). Next we sought to determine whether D7-pM T cells could also recognize whole melanoma cells expressing MART-1 and HLA-DRβ1*0101. As shown in FIG. 3, D7-pM T cells recognized all of three allogeneic melanomas tested which expressed both HLA-DRβ1*0101 and MART-1, but failed to recognize DR1 or MART-1 negative cells. In the same experiment, DR1-restricted CD4+ TIL 1558, specific for the TPImut antigen unique to 1558-mel, recognized 1558-mel but not the other tumors (39). Two repeat experiments yielded similar results (not shown). HLA-DR restriction of tumor recognition by T cells was confirmed with anti-MHC mAb blockade (not shown). Of interest, while D7-pM CD4+ T cells specifically reacted against intact DR1+, MART-1+ tumor cells, they failed to recognize DR1+ EBV-B cells pulsed with lysates of MART-1+ tumors. In the same experiment, CD4+ TIL 1558 recognized processed 1558-mel lysate and provided a positive control for exogenous pathway processing (39) (not shown). Thus, although MART-1 is a transmembrane protein, the pMART-1 epitope did not appear to be processed through the exogenous/endosomal route in these preliminary experiments. Future work will address the mechanism by which pMART-1 is processed intracellularly for presentation in the context of MHC class II molecules.

In summary, our demonstration of phosphopeptides associated with human MHC II molecules has revealed a new cohort of tumor antigens potentially recognizable by the immune system and therefore targetable by cancer immunotherapies. Although tumor-associated MHC class II-restricted phosphopeptides were previously thought to be degraded within the MHC II processing environment, recent technological advances have enabled us to identify a large number of phosphoepitopes from both melanoma and EBV-B cell lines. These may provide optimal targets for immunotherapy, since intracellular phosphoproteins associated with dysregulated signaling pathways play an important role in supporting the malignant cell phenotype and in providing escape mechanisms from anti-neoplastic agents. MART-1, a commonly expressed melanoma antigen containing MHC I- and II-restricted epitopes, has been a focus of cancer immunotherapeutics for over a decade and has now been revealed as a phosphoprotein recognizable by phosphopeptide-specific CD4+ T cells derived from a melanoma patient. Similarly, two phosphoproteins shown here to be sources for MHC II-restricted peptides, tensin-3 and insulin receptor substrate 2, have previously been shown to generate MHC I-restricted phosphopeptides (6). These findings suggest opportunities for developing combinatorial treatment approaches, using both MHC I- and II-restricted phosphopeptides as immunogens for raising potent polyvalent tumor-specific immunity.

Example 4

Materials And Methods

Cultured Cell Lines.

Human tissues were obtained through protocols approved by the Institutional Review Boards of the National Cancer Institute, NIH and the Johns Hopkins University School of Medicine. HLA genotypes of patients and cultured cell lines were determined by the NIH W.G. Magnuson Clinical Center HLA Laboratory (Bethesda, Md.) using sequence specific PCR techniques.

Isolation of HLA-DR-Associated Peptides.

To prepare cells for extraction of MHC-peptide complexes, growing cultures were harvested and spent medium was removed by centrifugation. Cells were washed twice in cold PBS, and dry cell pellets were snap frozen on dry ice and stored at −80° C. for subsequent lysis. HLA-DR/peptide complexes were immunoaffinity-purified from melanoma and EBV-B cells, and the associated peptides were extracted according to methods for MHC I-associated peptides (6) with minor modifications.

Phosphopeptide Enrichment.

Immunoaffinity-purified peptides were converted to methyl esters as previously described (6). A phosphopeptide standard, angiotensin II phosphate (100 fmole), was spiked into all samples prior to the esterification step to monitor the efficiency of the phosphopeptide enrichment.

Phosphopeptide Sequence Analysis by Tandem Mass Spectrometry.

Phosphopeptides were analyzed by nanoflow HPLC-microelectrospray ionization (nHPLC-µESI) coupled to either a hybrid linear quadrupole ion trap-Fourier-transform ion cyclotron resonance (LTQ-FT) mass spectrometer (Thermo Fisher Scientific, San Jose, Calif.) or an LTQ mass spectrometer (Thermo Fisher Scientific) modified to perform ETD. A precolumn loaded with phosphopeptides was connected with polytetrafluoroethylene tubing [0.06-in o.d. and 0.012-in i.d. (1 in=2.54 cm); Zeus Industrial Products, Orangeburg, S.C.] to the end of an analytical HPLC column (360-µm o.d. and 50 µm i.d.,) containing 7 cm of C18 reverse-phase packing material (5-µm particles, YMC). Phosphopeptides were eluted to the mass spectrometer at a flow rate of 60 nl/min with a gradient; 0-60% B in 20 min, 60-100% B in 5 min, [A=0.1 M acetic acid (Sigma-Aldrich) in $H_2O$; B=70% acetonitrile (Malinckrodt, Phillipsburg, N.J.) and 0.1 M acetic acid in $H_2O$. Parameters used to acquire ETD/MS/MS spectra in a data-dependent mode on the modified LTQ instrument have been described previously (40).

Data Analysis.

ETD and CAD MS/MS spectra of class II phosphopeptides were interpreted manually by J. S. and D. F. H. Data for the 175 sequences reported here were unambiguous. None of the sequences were assigned by software. Approximate copy/cell numbers for each phosphopeptide were determined by comparing peak areas of the observed parent ions to that of angiotensin II phosphate (DRV[pY]IHPF, 100 fmol) (Calbiochem) spiked into the sample mixture prior to peptide esterification and immobilized metal affinity chromatography. Specific functional and intracellular localization information for source proteins was determined from the Uniprot database, available on the internet. Source proteins for the identified phosphopeptides were searched in the Phospho-ELM database, available on the internet (41) to determine if the phosphoresidue was previously described or novel.

Generation of Human Phosphopeptide-Specific $CD4^+$ T Cells.

Peptide-specific $CD4^+$ T cells were raised by repetitive in vitro stimulation of PBMC from melanoma patients, as described (21). For candidate B-Raf phosphopeptides, patients were selected whose melanomas harbored the common T1799A (V600E) mutation. For pMART-1, selected patients expressed the HLA-DR1*0101 allele. Briefly, PBMCs were cultured in flat-bottom 96-well plates at $2\times10^5$ cells/well in RPMI 1640 plus 10% heat-inactivated human AB serum. GM-CSF (200 units/ml) and IL-4 (100 units/ml; PeproTech Inc., Rocky Hill, N.J.) were added on day 0 to generate dendritic cells as APCs, along with 25 µM peptide. Recombinant IL-2 120 IU/ml was added to lymphocyte cultures on day 7 and replenished every 4-7 days. For pMART-1 experiments, IL-7 and IL-15 were also added at 25 ng/ml at day 7 and replenished every 4-7 days. Thereafter, T cells were restimulated every 10-14 days with irradiated autologous PBMC or EBV-B cells pulsed with phosphopeptide, $1\times10^5$ feeder cells/well. Long-term $CD4^+$ T cell cultures were maintained in 120 IU/ml IL-2 and 20% conditioned medium from lymphokine activated killer cell cultures (B-Raf-specific T cells) or 120 IU/ml IL-2, 25 ng/ml IL-7 and 25 ng/ml IL-15 (pMART-1-specific T cells). $CD4^+$ TIL from melanoma patient number 1558, recognizing a unique HLA-DR1-restricted mutant TPI epitope, were used as controls in some experiments (39).

T Cell Recognition Assays.

To assess specific peptide recognition, $0.2\text{-}10\times10^5$ T cells/well were co-cultured overnight in flat-bottom 96-well plates with $1\times10^5$ EBV-B cells that had been pre-pulsed for 16-24 h with peptides at 20 µM (pB-Raf experiments) or 25 µM (pMART-1 experiments). Culture supernatants were then harvested, and GM-CSF or IFN-γ secretion by activated T cells was measured using commercially available ELISA kits (R&D Systems, Minneapolis, Minn.). When allogeneic EBV-B cells were used as APC to determine the MHC restriction of peptide-specific T cells, excess peptide was washed off before combining APC with T cells. Intact tumor cell recognition was tested by incubating T cells ($5\times10^4$/well) in microtiter plates with melanoma cells ($1\times10^5$/well) for 20 h. In some assays, mAb directed against MHC molecules were used to inhibit T cell reactivity, including W6/32 (IgG2a, anti-MHC class I, ATCC), L243 (IgG2a, anti-HLA-DR, ATCC), B7/21 (IgG1, anti-HLA-DP, Becton Dickinson, San Jose, Calif.) and SPVL3 (IgG2a, anti-HLA-DQ, Beckman Coulter, Marseilles, France). Final concentrations of mAb in blocking assays were 2.5 µg/ml for B7/21 and 20 µg/ml for the others. Surface expression of HLA-DR1 on tumor and EBV-B cells was confirmed by flow cytometry after staining with biotinylated anti-DR1, 10, 103 (One Lambda, Canoga Park, Calif.) and counter-staining with streptavidin-PE.

Example 5

Recognition of Phospho-MART-1 Peptides by CD4+ T Cells

Figure 7:
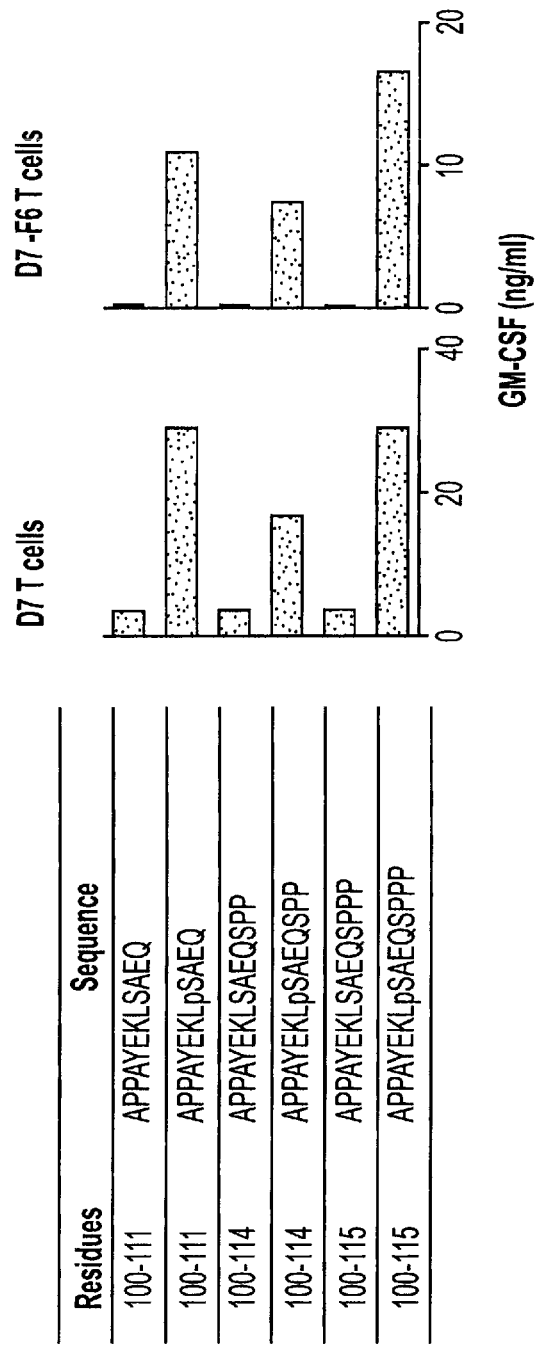
FIG. 7: Recognition of phosphorylated (SEQ ID NO: 14-16, in order as shown) vs. non-phosphorylated MART-1 peptides (SEQ ID NO: 22-24, in order as shown) by CD4+ T cells raised against pMART-100-111. Phospho-MART-specific D7 T cells or the D7-F6 T cell clone (5e4 cells/well) were co-incubated overnight with HLA-DR1+ 2048-EBV cells (1e5 cells/well) pre-pulsed with peptides (25 μM). GM-CSF secretion was measured by ELISA. Background GM-CSF secretion from T cells+APC+HA307-319 control peptide were 3.6 and <0.02 ng/ml, respectively. Results are representative of four separate experiments showing specific T cell recognition of phosphopeptides but not non-phosphorylated peptides.

The phosphate is a critical determinant for TCR recognition, as demonstrated using the D7 T cell line or a $CD4^+$ T cell clone (D7-F6) specific for pMART-1 (FIG. 7). These cells secreted the cytokine GM-CSF in response to phosphorylated MART-1 peptides pulsed onto DR1-expressing APCs, but not to their non-phosphorylated homologs.

Figure 5:
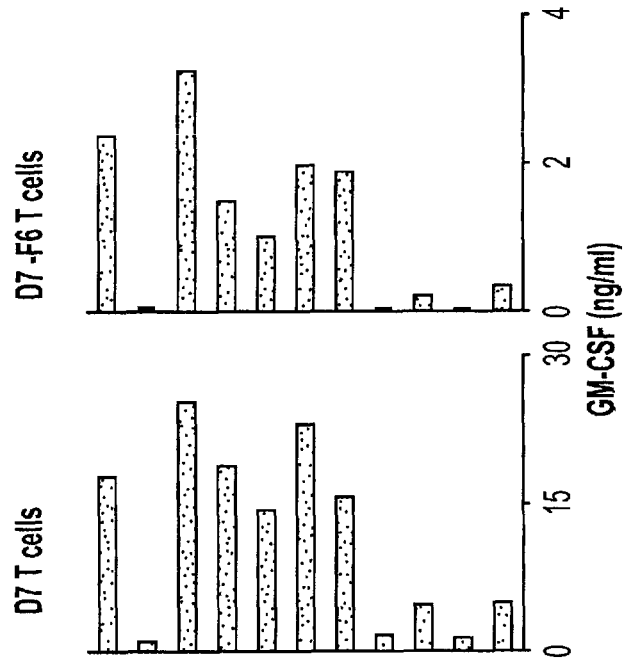
FIG. 5: Recognition of overlapping phospho-MART-1 peptides (SEQ ID NO:11-21) by the CD4+ D7 T cell culture and D7-F6 T cell clone, raised against pMART-100-111 by repetitive in vitro sensitization under limiting dilution conditions. T cells (5e4 or 1.2e4/well, respectively) were co-cultured overnight with HLA-DR1+ 2048-EBV cells (1e5/well) pre-pulsed with phosphopeptides (25 μM or 15 μM, respectively). GM-CSF secretion was measured by ELISA. Background GM-CSF secretion from T cells+APC+HA307-319 control peptide were 0.71 and <0.02 ng/ml, respectively. Results are representative of 4 separate experiments. Similar results were obtained with IFNγ secretion. *: Phosphopeptide eluted from HLA-DR molecules on 1363-mel. $: Phosphopeptide eluted from HLA-DR molecules on 2048 mel.
Figure 6:
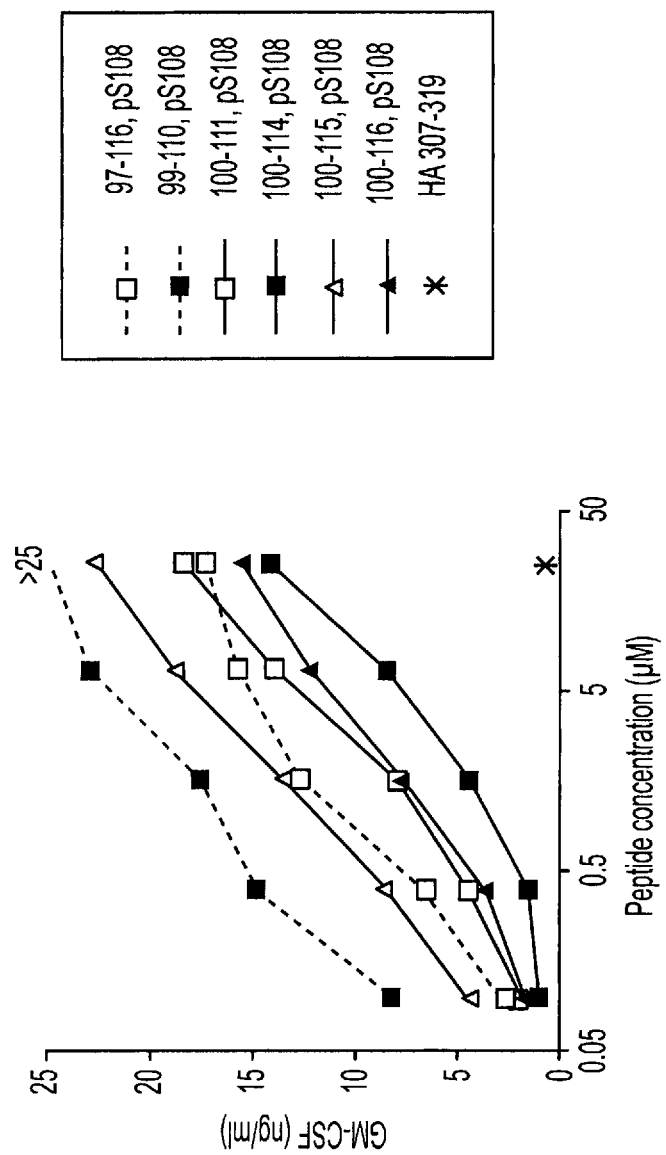
FIG. 6: Recognition of overlapping MART-1 phosphopeptides by CD4+ D7 T cells raised against pMART-1100-111. T cells (5e4/well) were co-cultured with peptide-pulsed HLA-DR1+ 2048-EBV cells (1e5/well) overnight. GM-CSF secretion was measured by ELISA. Background GM-CSF secretion from T cells+APC+HA307-319 control peptide (25 μM) was 0.7 ng/ml. Results are representative of 3 separate experiments. Similar results were obtained with IFNγ secretion.

Having established that phosphorylation is essential for TCR recognition, we next examined recognition of a series of synthetic overlapping phospho-MART-1 peptides, in order to identify other determinants of T cell reactivity (FIGS. 5 and 6). Similar to pMART-1$_{100-116}$ (SEQ ID NO:17), a series of naturally occurring C-terminally truncated phosphopeptides (pMART-1$_{100-115}$ (SEQ ID NO: 16), pMART-1$_{100-114}$ (SEQ ID NO: 15), pMART-1$_{100-111}$ (SEQ ID NO: 14)) and the synthetic peptide pMART-1$_{99-110}$ (SEQ ID NO: 13) were also capable of stimulating T cell reactivity, indicating that residues Gln111 through Tyr116 are not involved in critical interactions with TCR. Indeed, removal of Ser$_{112}$ and Pro$_{113}$ (compare pMART-1$_{100-114}$ (SEQ ID NO: 15) with pMART-1$_{100-111}$ (SEQ ID NO: 14)) resulted in an increase in T cell activa In sharp contrast to C-terminal residues Gln$_{111}$ to Tyr$_{116}$, N-terminal residues Leu$_{107}$ to Glu$_{110}$ contain important determinants for T cell recognition, besides the critical pSer$_{108}$ residue. Thus, removal of Glu110 (compare pMART-1$_{99-110}$ (SEQ ID NO: 13) with pMART-1$_{98-109}$ (SEQ ID NO: 12)) abrogated T cell stimulation.

Removal of N-terminal residues Ala100, Pro101, Pro102, and Ala103 (APPA motif) effectively abolished TCR recognition, as evident from comparing T cell stimulation by pMART-1$_{100-114}$ (SEQ ID NO: 15) versus pMART-1$_{103-114}$ (SEQ ID NO: 20), and pMART-1$_{100-115}$ (SEQ ID NO: 16) versus pMART-1$_{104-115}$ (SEQ ID NO: 21). These four N-terminal residues must include structural determinants required for TCR recognition.

REFERENCES

The disclosure of each reference cited is expressly incorporated herein.

1. Guinn B A, et al. (2007) Recent advances and current challenges in tumor immunology and immunotherapy. Mol Ther 15: 1065-1071.
2. Olsen J V, et al. (2006) Global, in vivo, and site-specific phosphorylation dynamics in signaling networks. Cell 127: 635-648.
3. Haluska F G, et al. (2006) Genetic alterations in signaling pathways in melanoma. Clin Cancer Res 12: 2301s-2307s.
4. Oka M, Kikkawa U (2005) Protein kinase C in melanoma. Cancer Metastasis Rev 24: 287-300.
5. Zarling A L, et al. (2000) Phosphorylated peptides are naturally processed and presented by major histocompatibility complex class I molecules in vivo. J Exp Med 192: 1755-1762.
6. Zarling A L, et al. (2006) Identification of class I MHC-associated phosphopeptides as targets for cancer immunotherapy. Proc Natl Acad Sci USA 103: 14889-14894.
7. Andersen M, et al. (1999) Phosphorylated peptides can be transported by TAP molecules, presented by class I MHC molecules, and recognized by phosphopeptide-specific CTL. J Immunol 163: 3812-3818.
8. Hogan K T, et al. (1998) The peptide recognized by HLA-A68.2-restricted, squamous cell carcinoma of the lung-specific cytotoxic T lymphocytes is derived from a mutated elongation factor 2 gene. Cancer Res 58: 5144-5150.
9. Larson J K, Otvos L, Jr., Ertl H C (1992) Posttranslational side chain modification of a viral epitope results in diminished recognition by specific T cells. J Virol 66: 3996-4002.
10. Monneaux F, Lozano J M, Patarroyo M E, Briand J P, Muller S (2003) T cell recognition and therapeutic effect of a phosphorylated synthetic peptide of the 70K snRNP protein administered in MR/lpr mice. Eur J Immunol 33: 287-296.
11. Otvos L, Jr., et al. (1996) The effects of post-translational side-chain modifications on the stimulatory activity, serum stability and conformation of synthetic peptides carrying T helper cell epitopes. Biochim Biophys Acta 1313: 11-19.
12. van Stipdonk M J, et al. (1998) T cells discriminate between differentially phosphorylated forms of alphaB-crystallin, a major central nervous system myelin antigen. Int Immunol 10: 943-950.
13. Yadav R, et al. (2003) The H4b minor histocompatibility antigen is caused by a combination of genetically determined and posttranslational modifications. J Immunol 170: 5133-5142.
14. Mohammed F, et al. (2008) Phosphorylation-dependent interaction between antigenic peptides and MHC class I: a molecular basis for the presentation of transformed self. Nat Immunol 9: 1236-1243.
15. Petersen J, et al. (2009) Phosphorylated self-peptides alter human leukocyte antigen class I-restricted antigen presentation and generate tumor-specific epitopes. Proc Natl Acad Sci USA 106: 2776-2781.
16. Gerloni M, Zanetti M (2005) CD4 T cells in tumor immunity. Springer Semin Immunopathol 27: 37-48.
17. Pardoll D M, Topalian S L (1998) The role of CD4+ T cell responses in antitumor immunity. Curr Opin Immunol 10: 588-594.
18. Engelhard V H, Altrich-Vanlith M, Ostankovitch M, Zarling A L (2006) Post-translational modifications of naturally processed MHC-binding epitopes. Curr Opin Immunol 18: 92-97.
19. Depontieu F, et al. (2008) Tumor-associated MHC II-restricted phosphopeptides: New targets for immune recognition. FASEB J 22: 1079.1071.
20. Davies H, et al. (2002) Mutations of the BRAF gene in human cancer. Nature 417: 949-954.
21. Sharkey M S, Lizee G, Gonzales M I, Patel S, Topalian S L (2004) CD4(+) T-cell recognition of mutated B-RAF in melanoma patients harboring the V599E mutation. Cancer Res 64: 1595-1599.
22. Viner N J, Nelson C A, Deck B, Unanue E R (1996) Complexes generated by the binding of free peptides to class II MHC molecules are antigenically diverse compared with those generated by intracellular processing. J Immunol 156: 2365-2368.
23. Marincola F, Stroncek D, Simonis T (1998) in HLA 1998, eds. Gjertson D W, Terasaki P I (American Society for Histocompatibilty and Immunogenetics, Lenexa), pp 276-277.
24. Lippolis J D, et al. (2002) Analysis of MHC class II antigen processing by quantitation of peptides that constitute nested sets. J Immunol 169: 5089-5097.
25. Blom N, Gammeltoft S, Brunak S (1999) Sequence and structure-based prediction of eukaryotic protein phosphorylation sites. J Mol Biol 294: 1351-1362.
26. Nimmerjahn F, et al. (2003) Major histocompatibility complex class II-restricted presentation of a cytosolic antigen by autophagy. Eur J Immunol 33: 1250-1259.
27. Dengjel J, et al. (2005) Autophagy promotes MHC class II presentation of peptides from intracellular source proteins. Proc Natl Acad Sci USA 102: 7922-7927.
28. Kageyama S, Tsomides T J, Sykulev Y, Eisen H N (1995) Variations in the number of peptide-MHC class I complexes required to activate cytotoxic T cell responses. J Immunol 154: 567-576.
29. Irvine D J, Purbhoo M A, Krogsgaard M, Davis M M (2002) Direct observation of ligand recognition by T cells. Nature 419: 845-849.

30. Engelhard V H, Brickner A G, Zarling A L (2002) Insights into antigen processing gained by direct analysis of the naturally processed class I MHC associated peptide repertoire. Mol Immunol 39: 127-137.
31. Coulie P G, et al. (1994) A new gene coding for a differentiation antigen recognized by autologous cytolytic T lymphocytes on HLA-A2 melanomas. J Exp Med 180: 35-42.
32. Kawakami Y, et al. (1994) Cloning of the gene coding for a shared human melanoma antigen recognized by autologous T cells infiltrating into tumor. Proc Natl Acad Sci U S A 91: 3515-3519.
33. Hoashi T, et al. (2005) MART-1 is required for the function of the melanosomal matrix protein PMEL17/GP100 and the maturation of melanosomes. J Biol Chem 280: 14006-14016.
34. Bioley G, et al. (2006) Melan-A/MART-1-specific CD4 T cells in melanoma patients: identification of new epitopes and ex vivo visualization of specific T cells by MHC class II tetramers. J Immunol 177: 6769-6779.
35. Godefroy E, et al. (2006) Identification of two Melan-A CD4+ T cell epitopes presented by frequently expressed MHC class II alleles. Clin Immunol 121: 54-62.
36. Larrieu P, Ouisse L H, Guilloux Y, Jotereau F, Fonteneau J F (2007) A HLA-DQ5 restricted Melan-A/MART-1 epitope presented by melanoma tumor cells to CD4+ T lymphocytes. Cancer Immunol Immunother 56: 1565-1575.
37. Marincola F M, Rivoltini L, Salgaller M L, Player M, Rosenberg S A (1996) Differential anti-MART-1/MelanA CTL activity in peripheral blood of HLA-A2 melanoma patients in comparison to healthy donors: evidence of in vivo priming by tumor cells. J Immunother Emphasis Tumor Immunol 19: 266-277.
38. Zarour H M, et al. (2000) Melan-A/MART-1(51-73) represents an immunogenic HLA-DR4-restricted epitope recognized by melanoma-reactive CD4(+) T cells. Proc Natl Acad Sci USA 97: 400-405.
39. Pieper R, et al. (1999) Biochemical identification of a mutated human melanoma antigen recognized by CD4(+) T cells. J Exp Med 189: 757-766.
40. Chi A, et al. (2007) Analysis of phosphorylation sites on proteins from Saccharomyces cerevisiae by electron transfer dissociation (ETD) mass spectrometry. Proc Natl Acad Sci USA 104: 2193-2198.
41. Diella F, Gould C M, Chica C, Via A, Gibson T J (2008) Phospho.ELM: a database of phosphorylation sites—update 2008. Nucleic Acids Res 36: D240-244.
42. Kawakami Y, et al. (1997) Production of recombinant MART-1 proteins and specific antiMART-1 polyclonal and monoclonal antibodies: use in the characterization of the human melanoma antigen MART-1. J Immunol Methods 202: 13-25.

The invention claimed is:

1. A composition comprising: an isolated phosphopeptide consisting of between 9 and 30 contiguous amino acids selected from SEQ ID NO:1 (MART-1) including motif YEKLSA (residues 104-109 of SEQ ID NO: 1) containing the serine at position 108 of MART-1, wherein the serine is phosphorylated, wherein the phosphopeptide binds to HLA-DR1; and an effective amount of an immune adjuvant.

2. The composition of claim 1, which is substantially free of other polypeptides.

3. The composition of claim 1, which is substantially free of human cells.

4. The composition of claim 1, wherein the phosphopeptide is in a complex with an HLADR1 molecule.

5. The composition of claim 4 wherein the complex is a tetramer.

6. The composition of claim 3 which comprises an admixture with one or more distinct phosphopeptides.

7. The composition of claim 6 wherein the one or more distinct phosphopeptides are melanoma-specific.

8. The composition of claim 4 wherein the HLA-DR1 molecule is HLA-DRB1*0101.

9. The composition of claim 1 wherein the isolated phosphopeptide consists of an amino acid sequence selected from the group consisting of: residues 97-116 (SEQ ID NO: 11), residues 99-110 (SEQ ID NO: 13), residues 100-111 (SEQ ID NO: 14), residues 100-114 (SEQ ID NO: 15), residues 100-115 (SEQ ID NO: 16), and residues 100-116 (SEQ ID NO: 17).

10. The composition of claim 5 which comprises a specific reagent to bring monomers or dimers together as a tetramer.

11. The composition of claim 5 which comprises biotin as a specific reagent to bring monomers or dimers together as a tetramer.

12. The composition of claim 5 which comprises (a) biotin and avidin or (b) biotin and streptavidin as specific reagents to bring monomer or dimers together as a tetramer.

13. The composition of claim 1 wherein the phosphopeptide consists of the amino acid sequence of SEQ ID NO: 14.

14. The composition of claim 8 wherein the complex is a tetramer.

15. A composition comprising: an isolated phosphopeptide consisting of between 9 and 30 contiguous amino acids selected from SEQ ID NO:1 (MART-1) including motif YEKLSA (residues 104-109 of SEQ ID NO: 1) containing the serine at position 108 of MART-1, wherein the serine is phosphorylated, wherein the phosphopeptide binds to HLA-DR1, and wherein the phosphopeptide is detectably labeled.

16. A composition comprising: an isolated phosphopeptide consisting of between 9 and 30 contiguous amino acids selected from SEQ ID NO:1 (MART-1) including motif YEKLSA (residues 104-109 of SEQ ID NO: 1) containing the serine at position 108 of MART-1, wherein the serine is phosphorylated, wherein the phosphopeptide binds to HLA-DR1, and wherein the phosphopeptide is bound to a solid support.

17. A composition comprising: an isolated phosphopeptide consisting of between 9 and 30 contiguous amino acids selected from SEQ ID NO:1 (MART-1) containing the serine at position 108 of MART-1, wherein the serine is phosphorylated, wherein the phosphopeptide binds to HLA-DR1, said phosphopeptide selected from the group consisting of residues 101-109 (SEQ ID NO:3), residues 102-110 (SEQ ID NO:4), residues 103-111 (SEQ ID NO: 5), residues 104-112 (SEQ ID NO: 6), residues 97-116 (SEQ ID NO: 11), residues 99-110 (SEQ ID NO: 13), residues 100-111 (SEQ ID NO: 14), residues 100-114 (SEQ ID NO: 15), residues 100-115 (SEQ ID NO: 16), and residues 100-116 (SEQ ID NO: 17); and an effective amount of an adjuvant.

18. The composition of claim 1 wherein the isolated phosphopeptide consists of an amino acid sequence selected from the group consisting of: residues 101-109 (SEQ ID NO:3), residues 102-110 (SEQ ID NO:4), residues 103-111 (SEQ ID NO: 5), residues 104-112 (SEQ ID NO: 6), residues 97-116 (SEQ ID NO: 11), residues 99-110 (SEQ ID NO: 13), residues 100-111 (SEQ ID NO: 14), residues 100-114 (SEQ ID NO: 15), and residues 100-115 (SEQ ID NO: 16).

19. The composition of claim 15 wherein the isolated phosphopeptide consists of an amino acid sequence selected from the group consisting of residues 101-109 (SEQ ID NO:3), residues 102-110 (SEQ ID NO:4), residues 103-111 (SEQ ID NO: 5), residues 104-112 (SEQ ID NO: 6), residues 97-116 (SEQ ID NO: 11), residues 99-110 (SEQ ID NO: 13), residues 100-111 (SEQ ID NO: 14), residues 100-114 (SEQ ID NO: 15), and residues 100-115 (SEQ ID NO: 16).

20. The composition of claim 16 wherein the isolated phosphopeptide consists of an amino acid sequence selected from the group of residues 101-109 (SEQ ID NO:3), residues 102-110 (SEQ ID NO:4), residues 103-111 (SEQ ID NO: 5), residues 104-112 (SEQ ID NO: 6), residues 97-116 (SEQ ID NO: 11), residues 99-110 (SEQ ID NO: 13), residues 100-111 (SEQ ID NO: 14), residues 100-114 (SEQ ID NO: 15), and residues 100-115 (SEQ ID NO: 16.

21. The composition of claim 17 wherein the isolated phosphopeptide consists of an amino acid sequence selected from the group consisting of residues 101-109 (SEQ ID NO:3), residues 102-110 (SEQ ID NO:4), residues 103-111 (SEQ ID NO: 5), residues 104-112 (SEQ ID NO: 6), residues 97-116 (SEQ ID NO: 11), residues 99-110 (SEQ ID NO: 13), residues 100-111 (SEQ ID NO: 14), residues 100-114 (SEQ ID NO: 15), and residues 100-115 (SEQ ID NO: 16).

* * * * *